United States Patent [19]

Tosoni et al.

[11] Patent Number: 4,788,281

[45] Date of Patent: Nov. 29, 1988

[54] DEXTRAN HEXONIC ACID DERIVATIVE, FERRIC HYDROXIDE COMPLEX AND METHOD MANUFACTURE THEREOF

[76] Inventors: Anthony L. Tosoni, 7 Green Briar Rd., Willowdale, Ontario, Canada, M2K1H4; Natu Patel, 54 Cottesmore Crescent, Markham, Ontario, Canada, L3R3X6; Kenneth Coelho, 585 Jane St., Apt. 401, Toronto, Ontario, Canada, M6S4A3

[21] Appl. No.: 568,124

[22] Filed: Jan. 4, 1984

[51] Int. Cl.$^4$ .................................................. C08B 37/02
[52] U.S. Cl. ...................................... 536/113; 536/112
[58] Field of Search ................. 536/113, 112; 424/180

[56] References Cited

U.S. PATENT DOCUMENTS

| | | | |
|---|---|---|---|
| 3,536,696 | 10/1970 | Alsop | 536/112 |
| 4,370,476 | 1/1983 | Usher et al. | 536/113 |

FOREIGN PATENT DOCUMENTS

| | | | |
|---|---|---|---|
| 1199951 | 7/1970 | United Kingdom | 536/112 |
| 1200902 | 8/1970 | United Kingdom | 536/113 |

*Primary Examiner*—Alan Siegel
*Attorney, Agent, or Firm*—I. Louis Wolk

[57] ABSTRACT

A novel hexonic acid derivative of dextran and a complex thereof with ferric hydroxide which complex is stable and non-toxic and has a high iron content are obtained under carefully controlled conditions by reacting dextran having a molecular weight range between 2000 and 6000 with sodium chlorite; and then reacting with ferric hydroxide to produce the desired complex.

5 Claims, No Drawings

DEXTRAN HEXONIC ACID DERIVATIVE, FERRIC HYDROXIDE COMPLEX AND METHOD MANUFACTURE THEREOF

BACKGROUND OF THE INVENTION

Dextran $(C_6H_{10}O_5)n$ is a polysaccharide polymer, containing a plurality of mainly alpha-1,6 linked glucopyranose or glucosyl units, obtained by the action of certain organisms upon sucrose by methods well known to the prior art. It is generally produced in the form of an aqueous solution of a mixture of polymers of various molecular weights.

Iron dextran has been developed and utilized as a satisfactory product for therapeutic use, primarily as an agent for correcting iron deficiencies in animals and humans by parenteral administration as by intravenous or intramuscular injection. This product has certain advantages deriving from low toxicity, low incidence of side reactions and effective rate of iron absorption. It is frequently prepared by forming a complex of dextran with colloidal ferric hydroxide.

Certain prior art patents describe ferric hydroxide complexes with dextran or other carbohydrate derivatives in efforts to achieve a desired high iron content, suitable stability and low toxicity. Illustrative of such art are U.S. Pat. No. 3,536,696 to Alsop and Bremner and British Pat. No. 1,200,902 to the same inventors. Their U.S. patent describes the formation of ferric hydroxide complexes with a dextran carboxylic acid formed by introducing a carboxylic acid group into a terminal unit of the dextran polymer to form a dextran heptonic acid. The Alsop et al. British patent relates to a procedure for forming the ferric hydroxide complex by controlling the rate of addition of alkali during complexing.

One disadvantage of conventional iron dextran complexes is the fact that it is difficult to obtain injectable stable complexes in colloidal solution with fairly high iron content; say more than 10%, and that as the iron content increases, the viscosity of the complex increases rapidly so that at higher iron content the higher viscosity impedes administration by injection and decreases the rate of absorption into animal tissues.

As described in U.S. Pat. No. 4,370,476, high iron dextran complexes are obtained by reacting dextran in a two stage oxidation process to produce a polycarboxylic acid dextran polymer which is then complexed with ferric hydroxide to obtain a stable colloidal solution compound of very fine particles of ferric hydroxide as a complex with the dextran polymer in which the elemental iron content may be from 10-20% or more.

Prior to the above mentioned patent, an attempt was made to produce stable ferric hydroxide complexes having a ferric iron content of over 10% by reacting the ferric hydroxide with a dextran polymer which had been modified by treatment with sodium hydroxide at elevated temperatures to produce a product which was alleged to include a dextran polymer having a carboxylic acid group formed on at least one terminal unit of the polymer. While such structure may have been formed in this reaction, it was also discovered that the alkali simultaneously attacked the dextran polymer to produce a number of low molecular weight and colored breakdown products which were difficult if not impossible to separate and which would prevent practical separation of the carboxylic acid derivative for complexing with iron.

This process is described in British Pat. No. 1199951, and although the example does describe a product having an iron content of 15.4%, as a practical matter it was found that complexes suitable for injection having an iron content of over 10% could not be achieved without extensive and impractical purification procedures which also reduced yields to non-commerical levels.

Inasmuch as the dextran polymer of commerce is in fact a mixture of polymers of various molecular weights, it was apparent that reaction with alkali would not be effective to introduce a substantial number of carboxylic acid groups into the polymer mixture to facilitate introduction of ferric iron into the complex to effect the desired increase in iron content.

Subsequently, the difficulties apparently encountered in the practice of the process of the aforesaid British Pat. No. 1199951 led to the development of the process and product described in U.S. Pat. No. 3,536,696, in which dextran was first converted to a heptonic acid derivative and then complexed with ferric hydroxide. Complexes containing up to 250 mg of elemental iron per ml of solution are stated to be obtained. While this process appears to be effective in producing high iron content complexes, it does entail the use of cyanides to produce the heptonic acid derivative with its consequent disadvantages.

SUMMARY OF THE INVENTION

Applicants have now made the surprising discovery that dextran can be oxidized by means of sodium chlorite under carefully controlled conditions to produce a derivative having a terminal carboxylic acid group and which capable of complexing with ferric hydroxide to produce stable injectable solutions of suitable viscosity having a high iron content of up to 20% or more.

Unexpectedly, the hexonic acid derivatives produced by this oxidation procedure are significantly more effective in producing high iron complexes than any which are obtained using other oxidizing agents as taught by the prior art or any obtained by alkali treatment.

It is noted that U.S. Pat. No. 4,370,476 refers to oxidation of aldehyde groups present or formed on the dextran molecule using bromine and indicates that other oxidizing agents such as sodium hypobromite, sodium bromite, chlorine, iodine, sodium hypochlorite, or sodium chlorite may also be used. In evaluating these oxidizing agents in the direct oxidation of dextran polymers in a molecular weight range of 2000–6000, it was found that only sodium chlorite, under specific conditions, could produce dextran derivatives from which high iron complexes of suitable viscosity could be obtained in a simple and effective manner in high yields.

In accordance with applicant's invention, low molecular weight dextran polymers within a selected molecular weight range in which the average molecular weight must be between about 2000 and 6000, are oxidized with sodium chlorite in aqueous solution at a pH between 2.5 and 4.5 and at a reaction temperature of about 20°–30° C., preferably at about 25° C. At a lower pH, hydrolysis of of the dextran is found to occur and at a higher pH, the oxidation does not proceed effectively; at lower temperatures, the reaction is too slow to be economic or effective, while at higher temperatures, chlorine dioxide is given off and wasted and depolymerization may occur. The proportions of sodium chlorite used are dependent upon the reducing power of the starting dextran.

During the oxidation procedure, the sodium chlorite is added to the solution of dextran having the desired molecular weight range until the reducing power of the resulting solution is equivalent to 10% glucose or less. Depending on the conditions of reaction, such as temperature, pH, etc., the amount of sodium chlorite used has varied from 65% to 130% of the weight of the dissolved dextran.

With respect to the preferred molecular weight range, it has been found that when the starting dextran has an average molecular weight range below about 2000, the resulting iron complexes are too toxic while above about 6000 m.w., the complexes are too viscous for use as an injectable material.

The mechanism of simple oxidation with sodium chlorite as described herein has been extensively studied as compared with the alkali treatment of dextran as described in British Pat. No. 1199951. The alkali treatment, which is essentially a degradation process, produces a number of complex reactions and simultaneous attack upon the dextran molecule takes place in several different ways. As a result, a number of very low molecular weight and discoloured products are created, along with a certain proportion of carboxylic acid derivatives which include meta and iso-saccharinic acid as contrasted with the simple and straight forward oxidation according to the present invention in which the dextran molecule is relatively unaffected other than to produce the desired hexonic acid derivative which is represented by terminal gluconic acid units in the polymer.

The products from sodium chlorite oxidation of the dextran polymers referred to under the conditions described above will contain terminal D-gluconic acid residues having the structure

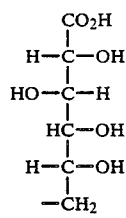
(1)

as contrasted with the meta-saccharinic acids produced by alkaline degradation of dextran represented by the structure

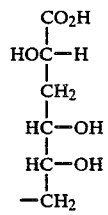
(2)

For reasons which are not clearly understood but which are believed to be necessarily related to the type of carboxylic acid derivative obtained, the dextran derivatives produced by the present process can be readily complexed with ferric hydroxide to product non-toxic stable injectable liquid complexes containing 10–20% iron or more.

The dextran derivatives are treated to remove inorganic ions by passage through mixed bed ion exchange resins or by dialysis, electrodialysis or ultra-filtration.

The iron complex may be formed by reacting the dextran carboxylic acid with purified ferric hydroxide in colloidal solution or suspension preferably at an initial pH of 8.0–8.5 at an elevated temperature, for example at a temperature range from boiling to autoclaving at about 120°, for 30 minutes. In this procedure the iron may be said to complex with the dextran derivative by the process of chelation. In practice the ferric hydroxide may be reacted with the oxidized dextran while in solution in the oxidizing reaction mixture preferably after adjustment of pH and concentration or the complexing may be carried out after the oxidized dextran polymer has been separated and redissolved as described in the examples below.

As described below the iron complex can be obtained in the form of a colloidal suspension in water with an elemental iron content of about 5–28% w/v in which the water content of the colloidal complex may vary but is generally in the range of 40–60% w/v. Such iron concentrations are obtained by concentration with evaporation, and the resulting suspensions have been found to be stable even with high iron concentrations. This permits the use of lesser proportions of dextran and lower non-volatile residues for the same amount of iron. The finished product as an extremely low free iron content with less than 0.25% of free ferric and ferrous iron and can easily tolerate usual autoclaving conditions such as 121° C. for 30 minutes for sterilization. If desired, the colloidal complex solution or suspension can be dried to powder and used as such or reconstituted in solution, but where it is to be ampouled to vialled for injection purposes it is preferable to recover the complex in water suspension for use in this form. The product also shows uniform dispersion and good tissue absorption at the injection site when tested on the legs of rabbits. Toxicity is low and the complex is found to be suitable for parenteral human and animal injection through intravenous tests on mice. The following examples illustrate the manner in which the invention is carried out.

EXAMPLE 1

To 1130 ml of an aqueous solution of 271 grams of low molecular weight dextran, at pH 3.0 was added with stirring, over a period of 1 hour, 163 grams of sodium chlorite. The temperature was maintained at 20°–25° C. The pH was kept at 3±0.2 with 12N hydrochloric acid. After complete addition, stirring was continued for 15 hours. The resulting solution was passed repeatedly through a mixed bed ion exchange resin column to a conductivity of 825 umhos. The pH was adjusted to 5.1 and the solution was evaporated to a dextran concentration of 21.5%.

To 604 ml of the above solution was added 1889 ml of a ferric hydroxide aqueous suspension containing 162.5 grams of elemental iron. The pH of the combined liquids was adjusted to 8.1 with 10% sodium hydroxide and the resulting liquid was evaporated to about 1000 ml. To it was added with stirring 1.5 liters of 92% isopropanol. The precipitate was allowed to settle, the supernatant was poured off and the precipitate was dissolved in 1500 ml of deionized water. The solution was evaporated to about 21% iron. The pH was adjusted to 6 with 10% sodium hydroxide, the chloride content to 0.9% with sodium chloride and the phenol content to 0.5% with 90% phenol solution. After filtration, the product was diluted with deionized water to the desired 20% iron. The relative viscosity was 16.8 at 37° C.

The resulting product was a colloidal suspension or solution of the desired dextran hexonic acid-ferric hydroxide complex, suitable for injection after appropriate sterilization and ampouling.

EXAMPLE II (10% IRON DEXTRAN)

To 714 ml. of an aqueous solution of 100 grams of low molecular weight dextran, was added with stirring, 93 grams of sodium chlorite over a period of 30 minutes. The pH was maintained at 3±0.2 and the temperature kept at 18°-20° C. pH adjustment was made with 12N Hcl.

After complete addition stirring was continued for 14 hours at room temperature maintaining the pH at 3±0.2.

The oxidized dextran was precipitated by the addition of 4 liters of methanol. The supernatant was decanted and the precipitate was dissolved in 400 ml deionized water.

The solution was passed repeatedly through a mixed ion-exchange resin column to a conductivity of 400 umhos. The pH was then adjusted to 5.5 with 10% sodium hydroxide and the solution was then concentrated by evaporation to 18.5% dextran.

To 65 ml of the above solution was added 126 ml of a suspension of ferric hydroxide, containing 10 grams of elemental iron. The pH of the combined materials was adjusted to 8.3 with 10% sodium hydroxide. It was then concentrated to about 80 ml. To it was added with stirring 120 ml of 95% isopropanol. The precipitate was allowed to settle, the supernatant was poured off and the precipitate was dissolved in 120 ml of deionized water. The resulting solution was evaporated to about 80 ml. The pH was adjusted to 6.4 with 1N, hydrochloric acid, the chloride content to 0.9% w/v with sodium chloride, and the phenol content to 0.5% w/v with 90% phenol solution.

After filtration, the colloidal dextran hexonic acid ferric hydroxide solution was diluted with water to contain 10% w/v iron. The relative viscosity was 4.8 at 37° C.

EXAMPLE II (PLANT BATCH, COUPLING OF IRON AT AUTOCLAVE TEMPERATURE) (20% IRON)

To 1000 liters of a soluton of low molecular weight dextran containing 224 kilos of dextran, was added with stirring over a period of 36 hours a total of 192 kgs. of sodium chlorite at room temperature. The pH was maintained at 3 to 3.5 by the addition of 12N hydrochloric acid. The resulting solution was passed through a mixed bed iron exchange resin column to a final conductivity of 560 umhos. The pH was then adjusted to 5.7 with 10% sodium hydroxide and it was then evaporated from a volume of about 4000 liters to about 650 liters.

To this solution was added 1665 liters of a suspension of ferric hydroxide in water containing 8.43% w/v elemental iron. The pH was adjusted to 6.1 with sodium hydroxide and it was then evaporated to 1600 liters, after which it was autoclaved at 15 p.s.i. for 60 minutes with stirring. It was again evaporated to a concentration of about 13% w/v iron. To this solution 700 liters of 97% isopropanol were added, with stirring. The precipitate was allowed to settle, the supernatant was removed and the precipitate was dissolved in 400 liters of deionized water. The pH was adjusted to 6.0 with sodium hydroxide and the resulting solution was evaporated to about 600 liters.

After pH, chloride content and phenol content adjustments and filtration the resultant solution contained 19.5% w/v iron with a relative viscosity of 13 at 37° C.

The product was the desired colloidal solution/suspension of the described dextran-hexonic acid-ferric hydroxide complex.

EXAMPLE IV

To 1400 liters low molecular weight dextran solution, containing 159.2 kgs. dextran, was added, over a period of 48 hours, a total of 130 kg. sodium chlorite at room temperature maintaining pH 2.9 to 3.2 by the addition of concentrated Hcl. The solution was then deionized through a mixed bed ion exchange resin column to a final conductivity of 420 umhos.

The pH of the solution was adjusted to 5.3, with sodium hydroxide and the solution evaporated to 840 liters (11.8% dextran).

To this was added 1227 liters ferric hydroxide suspension, containing 110 kg. of elemental iron. The pH was adjusted to 8.2 using a conc. NaOH solution, and the solution evaporated to approximately 14.0% Fe.

To this was added with stirring 880 liters 85% isopropanol the supernatant pumped out and the precipitate dissolved in approximately 800 liters deionized water and the solution evaporated to approximately 480 liters. (Fe concentration 21.4%). The pH of the solution was adjusted to 5.9, chloride content to 0.85% and phenol content to 0.50%. The iron dextran complex was filtered, diluted to 20.0% Fe with purified water, and then filtered through a 0.45 micron membrane filter.

The product (504 liters) which was the desired colloidal dextran hexonic acid-ferric hydroxide complex had a relative viscosity of 6.3 at 37° C. (Fe conc. 20.02%).

At 21.39% Fe, the relative viscosity was 8.09, and on concentration to 23.5% Fe, the relative viscosity was 18.1.

The colloidal solutions of the dextran hexonic acid ferric hydroxide complexes disclosed herein are intended for use as injectable iron solutions after appropriate vialling or ampouling and sterilization by autoclaving or the like, in accordance with procedures well known to the art. They had been found to be readily absorbed due to their relatively low viscosity in proportion to their high iron content and to be of little or low toxicity in animals.

We claim:

1. A dextran dexonic acid derivative having one or more terminal D-gluconic acid residues obtained by the oxidation of dextran having an average molecular weight of from about 2000 to 6000 with sodium chlorite at a pH of about 2.5–4.5 and at a temperature of about 20°–30° C.

2. A complex of the product of claim 1 with ferric hydroxide.

3. A process for producing a hexonic acid derivative of dextran which comprises oxidizing dextran having a molecular weight between about 2000 and 6000 with sodium chlorite in aqueous solution at a pH of about 2.5–4.5 and at a temperature of about 20°–30° C. and recovering the hexonic acid derivative produced thereby.

4. A process for the production of a ferric hydroxide complex with a dextran hexonic acid derivative which comprises reacting ferric hydroxide with the product produced by the process of claim 3.

5. A process according to claim 4 wherein ferric hydroxide is reacted with said dextran hexonic acid derivative in aqueous solution or suspension at an elevated temperature to produce a colloidal suspension of a complex thereof and concentrating the resulting suspension to a desired iron content.

* * * * *